United States Patent
Aladahalli et al.

(10) Patent No.: US 11,419,585 B2
(45) Date of Patent: Aug. 23, 2022

(54) METHODS AND SYSTEMS FOR TURBULENCE AWARENESS ENABLED ULTRASOUND SCANNING

(71) Applicant: GE Precision Healthcare LLC, Milwaukee, WI (US)

(72) Inventors: Chandan Kumar Mallappa Aladahalli, Bangalore (IN); Krishna Seetharam Shriram, Bangalore (IN); Vikram Melapudi, Bangalore (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 371 days.

(21) Appl. No.: 16/687,392

(22) Filed: Nov. 18, 2019

(65) Prior Publication Data
US 2021/0145411 A1 May 20, 2021

(51) Int. Cl.
*A61B 8/08* (2006.01)
*A61B 8/00* (2006.01)
*G06T 7/194* (2017.01)

(52) U.S. Cl.
CPC .......... *A61B 8/5276* (2013.01); *A61B 8/4461* (2013.01); *A61B 8/46* (2013.01); *G06T 7/194* (2017.01); *G06T 2207/20084* (2013.01); *G06T 2207/20112* (2013.01)

(58) Field of Classification Search
None
See application file for complete search history.

(56) References Cited

U.S. PATENT DOCUMENTS

| | | | |
|---|---|---|---|
| 2017/0164924 A1* | 6/2017 | Urabe | G06T 7/62 |
| 2017/0237983 A1* | 8/2017 | Adsumilli | H04N 21/23439 375/240.03 |
| 2019/0303720 A1* | 10/2019 | Karam | G06K 9/6262 |
| 2020/0323514 A1* | 10/2020 | Thienphrapa | A61B 8/12 |

OTHER PUBLICATIONS

"Structural similarity," Wikipedia Website, Available Online at https://en.wikipedia.org/wiki/Structural_similarity, Available as Early as Nov. 18, 2009, 8 pages.

* cited by examiner

*Primary Examiner* — Yi-Shan Yang
(74) *Attorney, Agent, or Firm* — McCoy Russell LLP

(57) ABSTRACT

Methods and systems are provided for turbulence monitoring during ultrasound scanning. In one example, during scanning with an ultrasound probe, a turbulence amount between two successive frames may be monitored, and in response to the turbulence amount at or above the higher threshold, deployment of the one or more image interpretation protocols may be stopped or delayed until the turbulence amount decreases below the higher threshold.

15 Claims, 6 Drawing Sheets

METHODS AND SYSTEMS FOR TURBULENCE AWARENESS ENABLED ULTRASOUND SCANNING

FIELD

Embodiments of the subject matter disclosed herein relate to medical imaging modalities, particularly to systems and methods for ultrasound imaging.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be displayed on a display device in real time or near real time.

One or more image interpretation protocols may be employed during scanning to assist a user in interpreting the scan images. An example interpretation protocol may include one or more artificial intelligence (AI) protocols based on deep learning models for identifying anatomical features in the ultrasound images and tracking the location of the identified anatomical features across multiple ultrasound images. Additionally or alternatively, one or more additional image interpretation protocols may be used during scanning, for example, for determining internal anatomical structure biometry, detecting anomaly, etc.

However, during ultrasound scanning, turbulence due to one or more of user generated probe motion and patient generated anatomical motion may occur. As a result image quality may degrade. Implementing the image interpretation protocols during turbulent scanning can reduce accuracy of structure identification, tracking, and anomaly detection performed by these protocols. Further, implementing the image interpretation protocols during scanning can give rise to labelling issues, such as placement, appearance, etc.

BRIEF DESCRIPTION

In one embodiment, a method for medical image processor, comprises: during an ultrasound scan, evaluating image quality between two scan images, and deploying one or more image interpretation algorithms only when the image quality is above a threshold.

In this way, by monitoring image quality during the ultrasound scanning, selective deployment of one or more image interpretation protocols is enabled. As a result, accuracy of image interpretation, anatomical structure biometry, and labelling with the interpretation protocols is improved.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
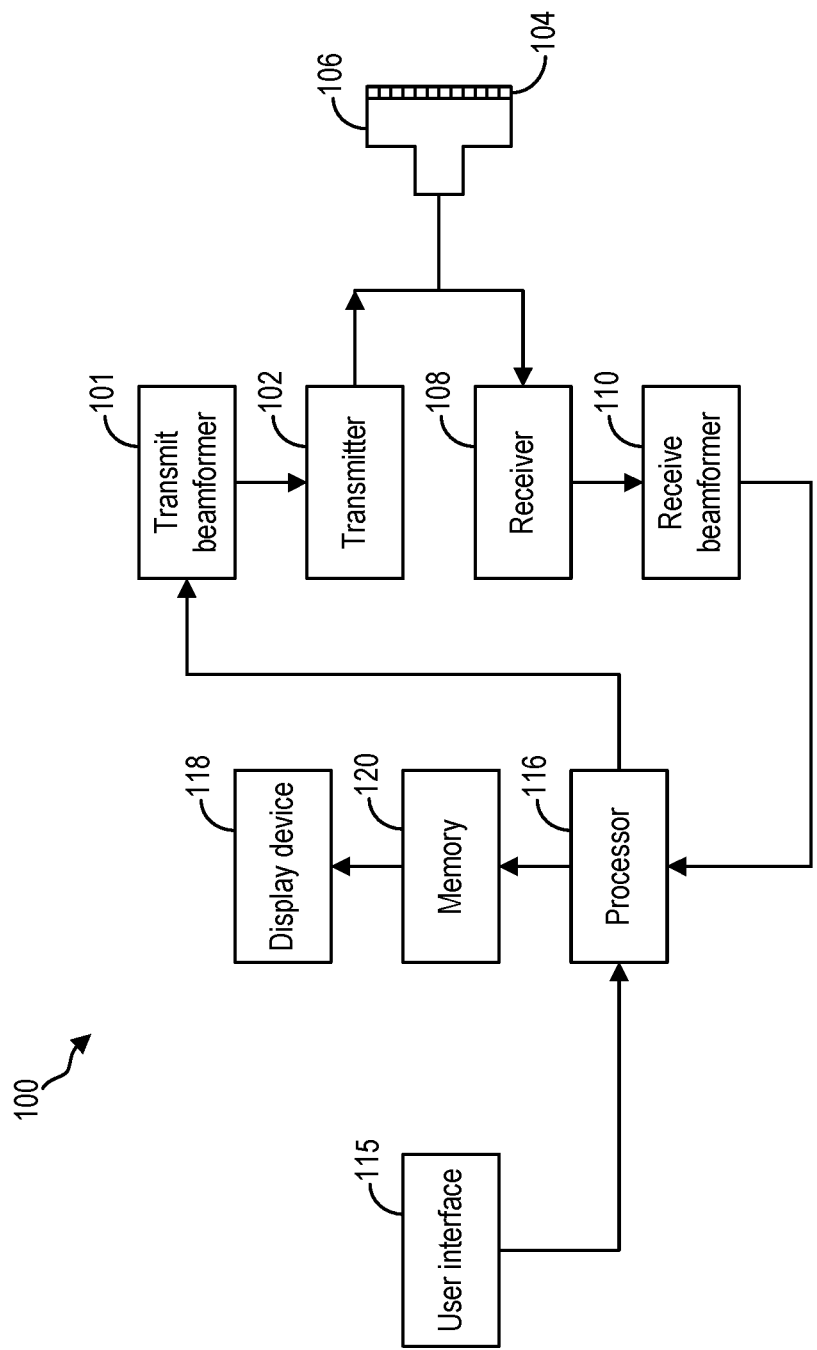
FIG. 1 shows a block diagram of an exemplary embodiment of an ultrasound system.
Figure 2:
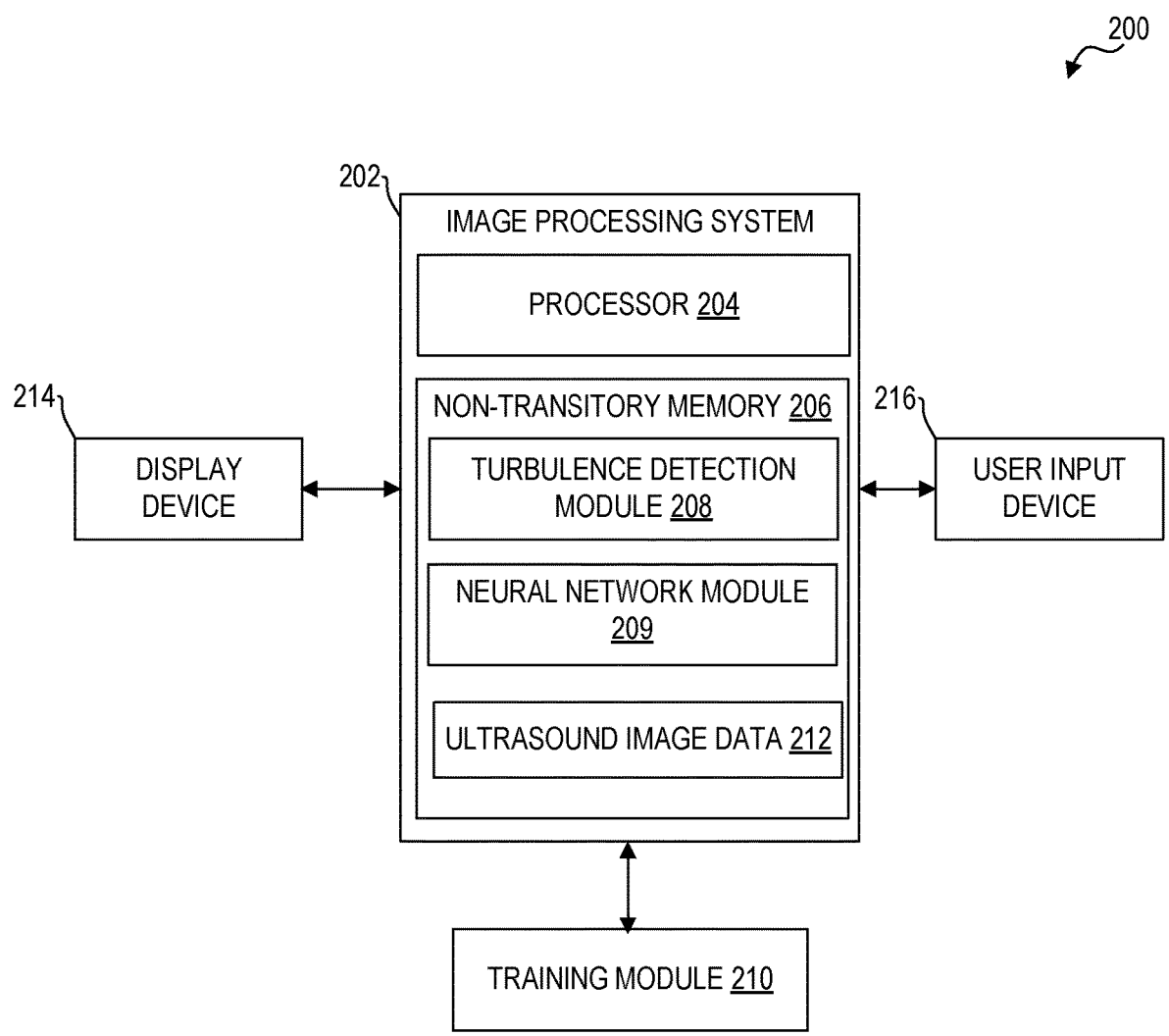
FIG. 2 is a schematic diagram illustrating a system for detecting turbulence and deploying one or more artificial intelligence protocols based on the detected turbulence, according to an exemplary embodiment.

The following description relates to various embodiments for ultrasound scanning. In particular, systems and methods for implementing one or more artificial intelligence protocols during ultrasound scanning. An example ultrasound system including an ultrasound probe, a display device, and an imaging processing system are shown in FIG. 1. Another exemplary image processing system that may be used with the ultrasound system of FIG. 1 is shown at FIG. 2. Via the ultrasound probe, ultrasound images may be acquired and displayed on the display device. During ultrasound scanning, depending on one or more of user action and a patient status, the scanning may be turbulent, which may decrease image quality. For example, turbulence during scanning may occur due to erratic probe movement by the user and/or due to patient movement, such as rapid breathing. Low image quality resulting from turbulence may cause downstream issues in image interpretation and analysis. Accordingly, a processor of the image processing system may be implemented to monitor turbulence and control deployment of one or more image interpretation and analysis algorithms. An exemplary method for turbulence monitoring and image interpretation algorithm deployment based on turbulence monitoring is described at FIG. 3. Specifically, during scanning, the processor may receive two or more scan images and determine current amount of turbulence by evaluating structural similarity between at least a reference image and a second image. Structural similarity is indicative of image quality and is inversely proportional to turbulence. For example, when structural similarity between the reference image and the second image is high, image quality of the second image with respect to the reference is high and the amount of turbulence is low. Similarly, when structural similarity between the reference image and the second image is low, image quality of the second image with respect to the reference image is low, and the amount of turbulence is high. As such, the amount of turbulence during a current scan process may be determined by evaluating structural similarity between at least two acquired images. A performance metric such as structural similarity index (SSIM) that determines similarity between two scan images may be used. Other performance metrics such as mean square error (MSE), peak signal to noise ratio (PSNR), Equivalent Number of Looks (ENL) and Edge preservation Index (EPI), and other variants of SSIM, such as multi-scale SSIM, complex wavelet SSIM, and three-component SSIM, are also within the scope of the disclosure. When the amount of turbulence increases above a threshold limit, the quality of ultrasound scanning is low, and hence the scan image quality is low. If artificial intelligence based algorithms are deployed during scanning when the amount of turbulence is greater than the threshold (that is, image quality is low), reliability on the algorithm to correctly identify and segment the anatomical structures, track the desired anatomical structures, and evaluate biometry during scanning is reduced. Thus, when the amount of turbulence is greater than the threshold, the processor may stop deployment of one or more image interpretation and analysis algorithms. Further, during a beginning time period of scanning, the turbulence monitoring may function as a gate-keeper, deploying one or more image interpretation and analysis algorithms only when the image quality is high and the amount of turbulence is below the threshold. Furthermore, in response to determining that the ultrasound scanning is performed with the amount of turbulence greater than the threshold, the processor may provide one or more alerts to the user via the user interface to indicate high turbulence and provide guidance (e.g., hold probe steady, hold breath, etc.) to assist the user in improving ultrasound scanning quality. Furthermore, in one exemplary embodiment, a rate of deployment of the one or more algorithms may be monitored, as described at FIG. 4, to further improve ultrasound scanning efficiency. An exemplary ultrasound scanning sequence with turbulence monitoring discussed at FIG. 3 is illustrated at FIG. 5.

Referring to FIG. 1 is a schematic diagram of an ultrasound imaging system 100 in accordance with an embodiment of the invention. The ultrasound imaging system 100 includes a transmit beamformer 101 and a transmitter 102 that drive elements 104 within a transducer array, or probe, 106 to emit pulsed ultrasonic signals into a body (not shown). According to an embodiment, the transducer array 106 may be a one-dimensional transducer array probe. However, in some embodiments, the transducer array 106 may be a two-dimensional matrix transducer array probe. Still referring to FIG. 1, the pulsed ultrasonic signals are back-scattered from features in the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. According to some embodiments, the probe 106 may contain electronic circuitry to do all or part of the transmit and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system.

A user interface 115 may be used to control operation of the ultrasound imaging system 100, including, to control the input of patient data, to change a scanning or display parameter, and the like. The user interface 115 may include one or more of the following: a rotary, a mouse, a keyboard, a trackball, hard keys linked to specific actions, soft keys that may be configured to control different functions, and a graphical user interface displayed on the display device 118.

The ultrasound imaging system 100 also includes a processor 116 to control the transmit beamformer 101, the transmitter 102, the receiver 108, and the receive beamformer 110. The processer 116 is in electronic communication with the probe 106. For purposes of this disclosure, the term "electronic communication" may be defined to include both wired and wireless communications. The processor 116 may control the probe 106 to acquire data. The processor 116 controls which of the elements 104 are active and the shape of a beam emitted from the probe 106. The processor 116 is also in electronic communication with a display device 118, and the processor 116 may process the data into images for display on the display device 118. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. In some embodiments, the processor 116 may be configured as graphical processing unit with parallel processing capabilities. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For example, an embodiment may acquire images at a real-time rate of 7-20 volumes/sec. The ultrasound imaging system 100 may acquire 2D data of one or more planes at a significantly faster rate. However, it should be understood that the real-time volume-rate may be dependent on the length of time that it takes to acquire each volume of data for display. Accordingly, when acquiring a relatively large volume of data, the real-time volume-rate may be slower. Thus, some embodiments may have real-time volume-rates that are considerably faster than 20 volumes/sec while other embodiments may have real-time volume-rates slower than 7 volumes/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a volume-rate of, for example, 10 Hz to 30

Hz. Images generated from the data may be refreshed at a similar frame-rate. Other embodiments may acquire and display data at different rates. For example, some embodiments may acquire data at a volume-rate of less than 10 Hz or greater than 30 Hz depending on the size of the volume and the intended application. A memory 120 is included for storing processed volumes of acquired data. In an exemplary embodiment, the memory 120 is of sufficient capacity to store at least several seconds worth of volumes of ultrasound data. The volumes of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical features and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. The image lines and/or volumes are stored and timing information indicating a time at which the data was acquired in memory may be recorded. The modules may include, for example, a scan conversion module to perform scan conversion operations to convert the image volumes from beam space coordinates to display space coordinates. A video processor module may be provided that reads the image volumes from a memory and displays an image in real time while a procedure is being carried out on a patient. A video processor module may store the images in an image memory, from which the images are read and displayed by display device 118.

In various embodiments of the present invention, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Ultrasound images acquired by ultrasound imaging system 100 may be further processed. In some embodiments, ultrasound images produced by ultrasound imaging system 100 may be transmitted to an image processing system, where in some embodiments, the ultrasound images may be segmented by a machine learning model trained using ultrasound images and corresponding ground truth output. As used herein, ground truth output refers to an expected or "correct" output based on a given input into a machine learning model. For example, if a machine learning model is being trained to classify images of cats, the ground truth output for the model, when fed an image of a cat, is the label "cat".

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training data set for training one or more machine learning models, wherein the machine learning models may be used to perform one or more steps of ultrasound image processing, as described below.

Referring to FIG. 2, image processing system 202 is shown, in accordance with an exemplary embodiment. In some embodiments, image processing system 202 is incorporated into the ultrasound imaging system 100. In some embodiments, at least a portion of image processing 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images/maps from the ultrasound imaging system or from a storage device which stores the images/data generated by the ultrasound imaging system. Image processing system 202 may be operably/communicatively coupled to a user input device 214 and a display device 216.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store neural network module 209, turbulence detection module 208, and ultrasound image data 212. Neural network module 209 may include one or more machine learning models, such as deep learning networks, comprising a plurality of weights and biases, activation functions, loss functions, gradient descent algorithms, and instructions for implementing the one or more deep neural networks to process input ultrasound images. Neural network module 209 may include trained and/or untrained neural networks and may further include training routines, or parameters (e.g., weights and biases), associated with one or more neural network models stored therein.

Image processing system 202 may be communicatively coupled to training module 210, which comprises instructions for training one or more of the machine learning models stored in neural network module 209. In one example, training module 210 includes instructions for receiving training data sets from ultrasound image data 212, which comprise sets of ultrasound images, associated ground truth labels/images, and associated model outputs for use in training one or more of the machine learning models stored in segmentation and tracking module 208. Training module 210 may receive ultrasound images, associated ground truth labels/images, and associated model outputs for use in training the one or more machine learning models from sources other than ultrasound image data 212, such as other image processing systems, the cloud, etc. In some embodiments, one or more aspects of training module 210 may include remotely-accessible networked storage devices configured in a cloud computing configuration. Non-transitory memory 206 may further store ultrasound image data 212, such as ultrasound images captured by the ultrasound imaging system of FIG. 1. For example, ultrasound image data 212 may store ultrasound images, ground truth output, iterations of machine learning model output, and other types of ultrasound image data. In some embodiments, ultrasound image data 212 may store ultrasound images and ground truth output in an ordered format, such that each ultrasound image is associated with one or more corresponding ground truth outputs.

In some embodiments, the non-transitory memory 206 may include components disposed at two or more devices, which may be remotely located and/or configured for coordinated processing. In some embodiments, one or more aspects of the non-transitory memory 206 may include remotely-accessible networked storage devices configured in a cloud computing configuration.

User input device 216 may comprise one or more of a touchscreen, a keyboard, a mouse, a trackpad, a motion sensing camera, or other device configured to enable a user to interact with and manipulate data within image processing system 31. In one example, user input device 216 may enable a user to make a selection of an ultrasound image to use in training a machine learning model, or for further processing using a trained machine learning model.

Display device 214 may include one or more display devices utilizing virtually any type of technology. In some embodiments, display device 214 may comprise a computer monitor, and may display ultrasound images. Display device 214 may be combined with processor 204, non-transitory memory 206, and/or user input device 216 in a shared enclosure, or may be peripheral display devices and may comprise a monitor, touchscreen, projector, or other display device known in the art, which may enable a user to view ultrasound images produced by an ultrasound imaging system, and view segmentation annotations of the ultrasound scan images, and/or interact with various data stored in non-transitory memory 206.

It should be understood that image processing system 202 shown in FIG. 2 is for illustration, not for limitation. Another appropriate image processing system may include more, fewer, or different components.

Figure 3A:
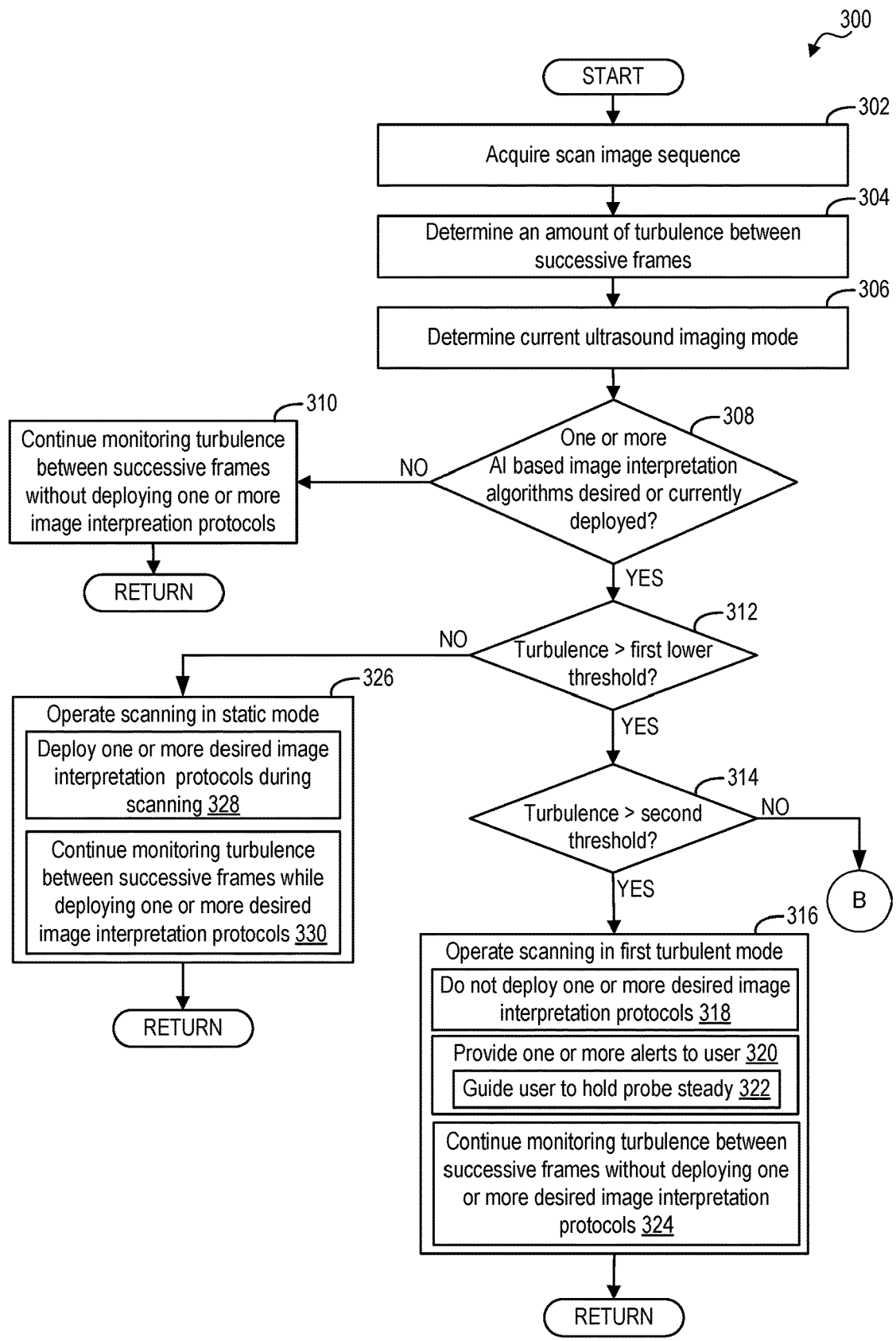
FIG. 3A shows a high-level flow-chart illustrating a method for detecting turbulence during ultrasound scanning and deploying one or more image interpretation protocols, according to an exemplary embodiment.

Turning to FIG. 3A, a high-level flow chart illustrating an example method 300 for monitoring turbulence during an ultrasound scan, and controlling deployment of one or more image interpretation and analysis protocols (alternatively referred to herein as image interpretation algorithm/protocol) based on the turbulence is shown. Method 300 is described with regard to the systems and components of FIGS. 1 and 2 although it should be appreciated that method 300 may be implemented with other systems and components without departing from the scope of the present disclosure. For example, method 300 may be stored as executable instructions in non-transitory memory, such as memory 120, and may be executed by a processor, such as processor 116, of the ultrasound imaging system 100, or may be implemented by one or more of the above disclosed systems, such as image processing system 202. In some embodiments, method 300 may be initiated by a medical personnel, such as a physician, or an operator, such as sonographers.

Method 300 begins at 302. At 302, method 300 includes acquiring a scan image sequence. Acquiring scan image sequence may include acquiring at least a first reference image and a second subsequent image. In some examples, the scan image sequence may be acquired over a period of time and may include more than two images.

Upon acquiring the scan image sequence, method 300 proceeds to 304. At 304, method 300 includes determining an amount of turbulence between at least two successive scan images (scan images are alternatively referred to herein as frames) for a duration of time. For example, the amount of turbulence may be calculated between the first reference image and the second subsequent image. In one embodiment, the amount of turbulence may be determined between successive frames in a sequence of frames for the duration of time. For example, the amount of turbulence may be determined between a first frame and a second frame, the second frame and a third subsequent frame, the third frame and a fourth subsequent frame, and so on. In another embodiment, the amount of turbulence may be determined between the first frame and each of the subsequent frames. For example, the amount of turbulence may be determined between the first reference frame and the second frame, the first reference frame and the third frame, the first reference frame and the fourth frame, and so on for the duration of time. In some embodiments, the amount of turbulence an average amount of turbulence between the reference frame and each of a desired number of successive frames for the duration of time. In one example, the reference frame may be based on an ultrasound imaging mode and the anatomical structure under evaluation.

The amount of turbulence may be based on a performance metric such as Peak Signal to Noise Ratio (PSNR), Mean Square Error (MSE), Structural Similarity Index Measure (SSIM), Equivalent Number of Looks (ENL) and Edge preservation Index (EPI). As an example, a high SSIM may indicate high structural similarity between the two frames, and thus, the amount of turbulence may be determined to be low. Thus, the amount of turbulence may be a function of a selected performance metric. Additionally, a turbulence rate for the duration of time may be determined. The turbulence rate may indicate a rate of change of structural similarity with respect to a reference frame in a sequence of images captured in the duration of time. Thus, the turbulence rate may be based on a rate of change of the selected performance metric. For example, if SSIM is used to measure turbulence, the turbulence rate may be based on the rate of change of SSIM over a period of time. The period of time may be selected based on periodicity of motion of the anatomical structure under examination. In some examples, the turbulence rate may be based on a frequency of structural difference indicated by the performance metric selected in the sequence of images.

Next, at 306, method 300 includes determining a current imaging mode. The current ultrasound imaging mode may be determined according to user input received at a user interface of the ultrasound system, such as user interface 115 of FIG. 1. An operator of the ultrasound system may select an imaging mode and/or protocol via the user interface, or otherwise enter input indicating a desired ultrasound imaging mode and/or desired imaging protocol. Example ultrasound imaging modes may include B-mode imaging, Doppler imaging, M-mode imaging, and the like.

Further, in some examples, the imaging mode may be based on the ultrasound imaging protocol. Example ultrasound imaging protocols may include cardiac imaging protocols (e.g., echocardiograms), abdomen imaging, fetal imaging, renal imaging, and/or other anatomy-specific protocols. Additionally, some example ultrasound imaging protocols may be based on a type of procedure being performed along with or during the imaging, such as a resuscitation protocol, needle biopsy protocol, etc. The imaging mode and/or protocol may dictate which type of ultrasound probe is used, how the ultrasound probe is controlled during the imaging session (e.g., signal frequency, gain, beam focus, etc.), how the acquired image information is processed, and/or what types of images the operator is to acquire during the imaging session, which may include how the operator is to position and control the ultrasound probe during the imaging session. In some examples, additionally, the user may indicate a desired exam type. For example, a list of possible exam types may be displayed, including internal organs, muscle tissues, vessels, tendons, etc. and the operator may click on the desired exam type, instructing the processor to load settings suitable for the type of exam.

Next, at 308, method 300 includes determining if one or more image interpretation protocols are desired or currently deployed. Specifically, method 300 may determine if one or more artificial intelligence based algorithms are deployed. Artificial intelligence based algorithms may include one or more of machine learning algorithms and deep learning algorithms that enable a user to interpret, analyze, and/or evaluate the ultrasound scan images. Example deep learning and machine learning algorithms may include one or more of segmentation algorithms, tracking algorithms, biometric algorithms, and classification algorithms. It will be appreciated that other artificial intelligence based algorithms for medical image processing are also within the scope of the disclosure.

If artificial intelligence algorithms are not deployed, the answer at 308 is NO, method 300 proceeds to 310. At 310, method 300 may continue to monitor turbulence based on the selected structural similarity metric as discussed above without deploying one or more artificial intelligence algorithms for image interpretation and analysis. In one embodiment, the ultrasound scanning may be performed without deploying one or more artificial intelligence algorithms. However, in some embodiments, one or more other image processing protocols that are not based on artificial intelligence may be deployed to assist the user in interpreting the scan images. The one or more other image processing protocols may include image quality improvement protocols. Method 300 may then return to continue to acquire scan sequences and determine turbulence for the acquired sequence.

Returning to 308, if one or more artificial intelligence based algorithms are desired or currently deployed, method 300 proceeds to 312. At 312, method 300 includes determining if the amount of turbulence is greater than a first lower threshold. The first lower threshold may be a threshold indication for steady state scanning. When the amount of turbulence is below the first lower threshold, the scanning performance is in high, and thus the image quality is high. As a result, the structural similarity between successive frames is high and the amount of turbulence is low. Thus, if the amount of turbulence is not greater than the first lower threshold, the answer at 312 is NO, and method 300 proceeds to 326.

At 326, method 300 includes operating the ultrasound scanning in a static mode, wherein the movement due to one or more of probe and anatomical structure is less. Operating the ultrasound scanning in the static mode may include, at 328, deploying the one or more desired image interpretation algorithms during scanning. The image interpretation protocols may include artificial intelligence based algorithms including deep learning algorithms and machine learning algorithms for image interpretation, analysis, and evaluation. Additionally, high-level image processing protocols that can be implemented without employing deep-learning models may be deployed. In one example, when a deep neural network based algorithm is deployed, the acquired scan image may be used as input to the neural network model, and corresponding output scan image may be obtained and displayed to the user. For example, if a deep neural network based segmentation algorithm is deployed, the acquired scan image may be used as input to the segmentation algorithm, and the output may be a segmented scan image of the acquired image including segmentations of the various internal anatomical structures visible in the scan image.

Further, at 330, method 300 includes continuing turbulence monitoring between successive frames of the acquired sequence while deploying one or more desired image interpretation protocols. Method 300 then returns.

Returning to 312, if the turbulence is at or greater than the first lower threshold, method 300 proceeds to 314. At 314, method 300 includes determining if the turbulence is greater than a second higher threshold. The second higher threshold may be greater than the first lower threshold. Further, the second higher threshold may be an indication of a limit for steady state scanning. For example, during scanning, movement due to steady internal physiological processes may be observed as steady state movements. When the amount of turbulence is below the second higher threshold, the relatively higher turbulence compared to static scan may be due to steady physiological movements. The steady state movement may be periodic. However, when the amount of turbulence is greater than the second higher threshold, the scanning turbulence may be due to rough irregular probe movement caused by the user, and the image quality may be low. As a result, structural similarity between the reference frame and the subsequent frame may be low, and consequently the performance metric may have a lower value when the amount of turbulence is high. Accordingly, if the amount of turbulence is greater than the second higher threshold, the answer at 314 is YES, and method 300 proceeds to 316.

At 316, method 300 includes operating the scanning in a first turbulent mode, wherein the image quality is low, and the amount of turbulence between successive frames is greater than the second higher threshold. When the amount of turbulence is greater than the second higher threshold, deploying image interpretation protocols may cause difficulty in labelling, tracking, and less accurate segmentation of the internal structure. Accordingly, operating the scanning in the first turbulence mode includes at 318, performing the scanning without deploying any of the one or more desired image interpretation protocols. Further, operating the scanning in the first turbulent mode includes, at 320, providing one or more alerts to the user. The one or more alerts may include, at 322, a guidance indication to the user to hold the probe steady. In one example, the guidance may be via a visual indication displayed at the user interface communicatively coupled to the ultrasound imaging system. In another example, additionally or alternatively, audible alerts may be provided.

Furthermore, operating the scanning in the first turbulent mode includes, at 324, continuing turbulence monitoring between successive frames of the acquired sequence without deploying one or more desired image interpretation protocols. In one embodiment, operating scanning in the first turbulent mode may include not deploying any image interpretation and analysis algorithm (including AI based and non-AI based image interpretation and analysis algorithms) during the ultrasound scanning. In some examples, when the turbulence is greater than the second threshold, medical image quality improvement algorithms, such as denoising, contrast enhancement, etc., may be deployed. Method 300 then returns.

In this way, turbulence monitoring algorithm based on method 300 acts as a gatekeeper for one or more image interpretation and analysis algorithms by deploying the one or more image interpretation and analysis algorithms only when the a performance metric of ultrasound scanning is high. That is, when structural similarity between the reference frame and one or more successive frames is high, and the amount of turbulence is low, one or more image interpretation and analysis algorithms may be deployed.

Figure 3B:
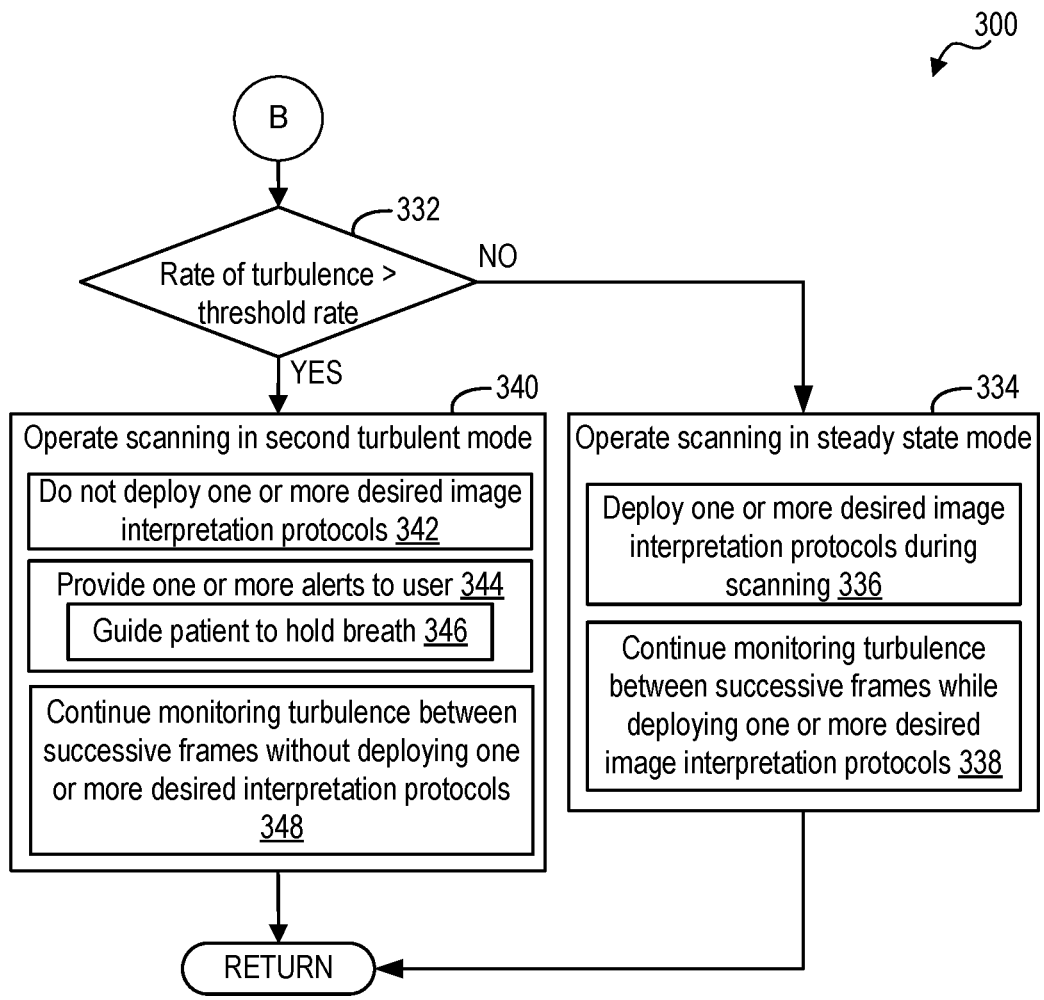
FIG. 3B is a continuation of FIG. 3A

Returning to 314, if the turbulence is not greater than the second threshold, the answer at 314 is NO, and method 300 proceeds to 332 at FIG. 3B. At 332, method 300 includes evaluating if a rate of turbulence is greater than a threshold rate. The turbulence rate may be based on rate of change of image quality in a frame sequence with respect to the reference frame over the duration of time. That is, turbulence rate may be a frequency of change of image quality over a sequence of scan images in the duration of time. For example, during ultrasound scanning, periodic motion due to physiological processes may occur and may be visible during the scan. When a reference frame is selected, the performance metric may reach a peak each time the scan image matches the reference frame. Consequently, for the frame sequence, the performance metric may exhibit a sinusoidal pattern with peaks coinciding with the reference frame images. Thus, the rate of turbulence may be based on the frequency of oscillation of the performance metric observed over the period of time during scanning. During steady state conditions, for example, during normal breathing by the patient, the rate of turbulence may be within the threshold rate and hence, an AI based algorithm may be deployed during scanning. However, when breathing is rapid, the rate of turbulence may be greater than the threshold rate, which may cause issues in one or more of labelling, tracking, segmentation, and classification, when AI based image interpretation and analysis algorithms are deployed. Thus, if the turbulence rate is at or greater than the threshold rate, the answer at 332 is YES, method 300 proceeds to 340. At 340, method 300 includes operating scanning in a second turbulent mode. Operating the scan in the second turbulent mode includes, at 342, performing the ultrasound scan without deploying one or more desired image interpretation algorithms. Specifically, artificial intelligence based algorithms may not be deployed when the rate of turbulence is greater than the threshold. Further, if one or more desired image interpretation algorithms are currently deployed, the implementation of the currently deployed image interpretation algorithms may be stopped and the scanning may proceed without deploying the one or more desired image interpretation algorithms. In some embodiments, as indicated above, medical image quality improvement algorithms, such as denoising, contrast enhancement, etc., may be deployed when the rate of turbulence is greater than the threshold rate. It may be noted that during scanning, when the amount of turbulence is below the lower threshold (that is, when operating in the static mode as discussed at step 326), the turbulence rate may not be monitored, and the one or more image interpretation and analysis algorithms may be deployed irrespective of turbulence rate.

Further, operating the scan in the second turbulent mode includes, at 344, providing one or more alerts to the user, which may include at 346, guiding the patient to hold breath for a desired duration. In one example, the guidance may be via one or more of a visual indication displayed at the user interface communicatively coupled to the ultrasound imaging system, and an audible alert.

Further, operating the scan in the second turbulent mode includes, at 348, continuing turbulence monitoring between successive frames of the acquired sequence or between the reference frame and each of one or more successive frames as discussed above, without deploying one or more desired image interpretation protocols. Method 300 then returns.

Returning to 332, if the turbulence rate is not greater than the threshold rate, the observed higher turbulence may be due to steady-state motion of an internal anatomical structure, and the answer at 332 is NO. Method 300 then proceeds to 334. At 334, method 300 includes operating the scanning in a steady-state mode. Operating the scanning in the steady-state mode includes at 336, deploying one or more desired image interpretation protocols during scanning. Further, at 336, method 300 includes continuing turbulence monitoring between successive frames of the acquired sequence or between the reference frame and each of one or more successive frames while deploying one or more desired image interpretation protocols. Method 300 then returns.

In this way, turbulence during ultrasound scanning may be monitored, and only when the turbulence is within the second threshold amount and the rate of turbulence is within the threshold rate, one or more artificial intelligence based algorithms for image interpretation and analysis may be deployed. In one embodiment, deploying one or more artificial intelligence based algorithms for image interpretation and analysis may include using the ultrasound scan image or a sequence of images as inputs into a deep learning model, which may then perform one or more of segmentation, identification, tracking, labelling, and classification on the input image(s). By deploying artificial intelligence based algorithms only when the image quality is high (that is, turbulence less than the threshold) the one or more tasks performed by the algorithm, such as segmentation, identification, tracking, labelling, classification etc., may have higher accuracy and efficiency. Further, by monitoring turbulence, guidance may be provided to the user to either hold probe steady or ask patient to hold breath, which improves scanning performance by the user. Furthermore, by monitoring rate of turbulence (that is, frequency of change of image quality over a sequence of scan images is within a threshold frequency) along with the turbulence amount, the cause of turbulence (e.g., due to rapid breathing by patient or due to unsteady probe movement by the user) may be determined, and appropriate guidance may be provide to the user (e.g., hold breath versus hold probe steady). In one example, the guidance may be via a visual indication displayed at a user interface communicatively coupled to the ultrasound imaging system. In another example, additionally or alternatively, audible alerts may be provided.

In another embodiment, the turbulence monitoring may be based on the amount of turbulence alone. In such embodiments, when the turbulence amount is at or greater than the second higher threshold, the one or more desired image interpretation algorithms may not be deployed or any currently running algorithms may be stopped until the turbulence amount decreases below the second higher threshold. While the above embodiments are described with two thresholds for turbulence monitoring, including the first lower threshold and the second higher threshold, embodiments where a single threshold is used for turbulence monitoring are also within the scope of the disclosure.

Further, as discussed above, the amount of turbulence is based on an image quality metric, such as SSIM, variants of SSIM, MSE, PSNR, etc. Therefore, in another embodiment, during ultrasound scanning, one or more image interpretation and analysis algorithms may be deployed only when an image quality between two successive scan images is greater than a threshold. Further, image quality may be continued to be monitored during scanning while deploying the one or more image interpretation and analysis algorithms, and when the image quality drops to the threshold or decreases below the threshold, deployment of the one or more image interpretation and analysis algorithms may be stopped. In one example, the one or more image interpretation and analysis algorithms may include but not limited to deep learning based algorithms such as deep neural network implemented segmentation, tracking, labelling, identification, and classification algorithms.

Figure 4:
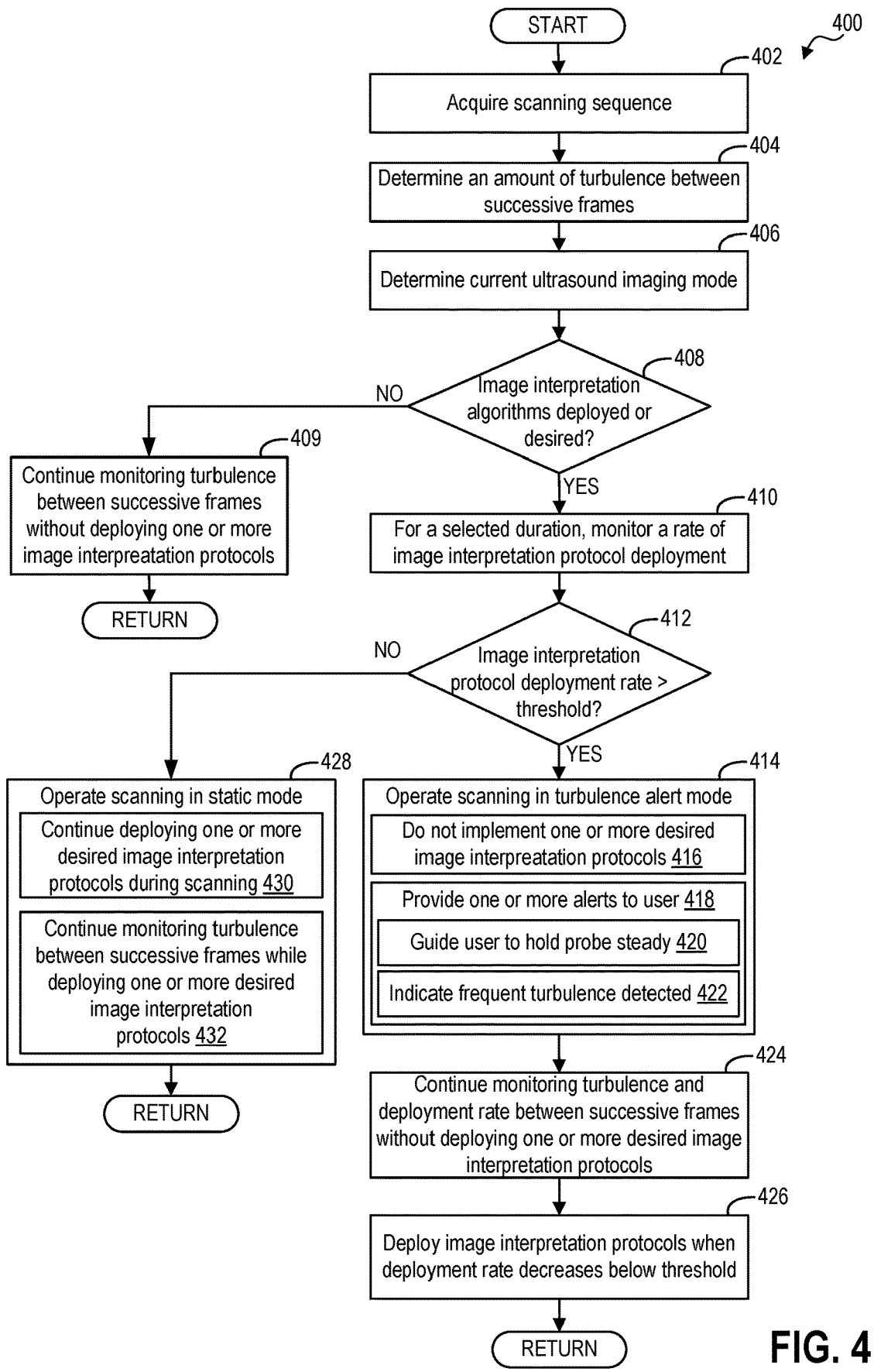
FIG. 4 shows a high-level flow chart illustrating a method for deploying one or more image interpretation protocols during ultrasound scanning based on a deployment rate; according to an exemplary embodiment.
Figure 5:
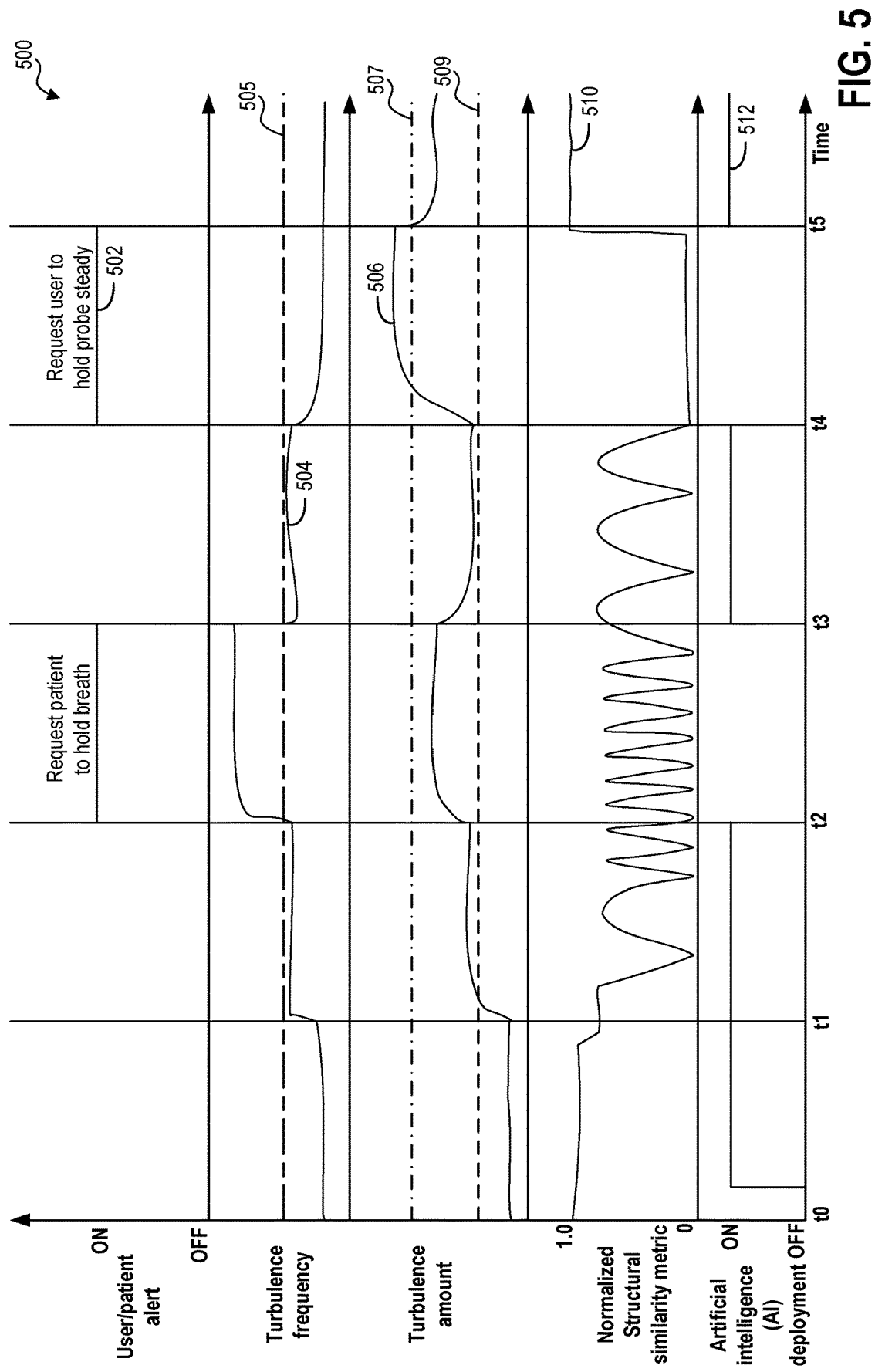
FIG. 5 shows an exemplary sequence for deploying one or more artificial intelligence protocols for interpreting scan images during ultrasound scanning, according to an exemplary embodiment.

Turning to FIG. 4, a flow chart for a high-level method 400 for evaluating deployment of one or more image interpretation algorithms based on previous deployment rate is shown. Method 400 is described with regard to the systems and components of FIGS. 1 and 2 although it should be appreciated that method 400 may be implemented with other systems and components without departing from the scope of the present disclosure. For example, method 400 may be stored as executable instructions in non-transitory memory, such as memory 120, and may be executed by a processor, such as processor 116, of the ultrasound imaging system 100, or may be implemented by one or more of the above disclosed systems, such as image processing system 202. In some embodiments, method 400 may be initiated by a medical personnel, such as a physician, or an operator, such as sonographers.

Method 400 begins at 402. Steps 402 through 406 are similar to steps 302 to 306 at FIG. 3A, and thus, will not be repeated for the sake of brevity. Briefly, a scanning sequence may be acquired, the amount of turbulence, the rate of turbulence, and the current imaging mode as discussed above with respect to method 300 may be determined.

Next, method 400 proceeds to 408. At 408, method 400 includes determining if one or more image desired image interpretation algorithms are desired or currently deployed. If the one or more image interpretation algorithms are not desired or currently deployed, the answer at 408 is NO, and method 400 proceeds to 409. At 409, method 400 may continue to monitor turbulence based on the structural similarity metric as discussed above without deploying one or more image interpretation protocols. Method 400 may then return to continue to acquire scan sequences and determine turbulence for the acquired sequence.

If the one or more image interpretation algorithms are not desired or currently deployed, the answer at 408 is YES, and method 400 proceeds to 410. At 410, method 400 includes monitoring a rate of image interpretation algorithm deployment (also referred to herein as algorithm deployment rate). Specifically, monitoring the algorithm deployment rate includes determining the rate at which the image interpretation algorithm deployment is switched ON and OFF over a scanning period. The scanning period for monitoring algorithm deployment rate may be chosen based on the current scan frame. Specifically, the scanning period for monitoring algorithm deployment rate may be a duration before the current scan frame, and may include the time period for the current scan frame.

For example, as discussed above with respect to FIG. 3, during one or more turbulent scanning conditions including one or more of scanning conditions when the amount of turbulence at or greater than the second threshold (e.g., due to unsteady probe movement by the user) and when the rate of turbulence is at or greater than the threshold rate (e.g., due to rapid breathing by the patient), the one or more desired image interpretation algorithms, such as AI based algorithms, may be turned OFF. When the turbulence decreases below the second threshold amount and the rate of turbulence is below the threshold, the one or more desired image interpretation algorithms may be turned ON. Thus, during ultrasound scanning, depending on the turbulence caused by user and/or the patient, the AI based image interpretation algorithms may be constantly turned ON and OFF. Thus, if the AI based algorithm deployment is constantly turned ON and OFF, the rate of image interpretation algorithm deployment may be higher, and vice-versa.

Next, upon determining the algorithm deployment rate, method 400 proceeds to 412. At 412, method 400 includes determining if the algorithm deployment rate is greater than a threshold. If YES, the AI based algorithms are constantly turned ON and OFF, which indicates turbulent scanning conditions, which may be due to low image quality resulting from one or more of patient and probe movements. Switching AI based algorithms ON and OFF during such turbulent scanning conditions, may reduce ultrasound scanning efficiency. Accordingly, when the algorithm deployment rate is greater than the threshold, method 400 proceeds to 414. At 414, method 400 includes operating scanning in a turbulence alert mode. For example, image interpretation protocols may be repeatedly turned off and on, when the image quality is not consistently high. Thus, operating the scan in the turbulence alert mode includes, at 416, operating the scan without implementing one or more desired image interpretation protocols. In one embodiment, when the algorithm deployment rate is greater than the threshold deployment rate, the ultrasound scan may be performed without deploying the one or more image interpretation algorithms even when the amount of turbulence is less than the second higher threshold or the first lower threshold. Thus, deployment of image interpretation algorithms may be delayed until the deployment rate (number of times the image interpretation algorithms are turned ON and OFF during a scanning period) decreases below the threshold.

Further, scanning in the turbulence alert mode includes, at 418, providing one or more alerts to the user, which may include, at 420, guiding the user to hold the probe steady. Further, at 422, an indication that frequent turbulence is detected may be provided.

In some embodiments, certain image interpretation protocols that may be used to improve guidance to the user but does not need higher quality image sequences may be deployed. For example, a high-level indication of the current scan plane with respect to the entire human anatomy may be provided.

Next, method 400 proceeds to 424. At 424, method 400 includes continuing turbulence monitoring between successive frames of the acquired sequence without deploying one or more desired image interpretation protocols. Next, at 426, method 400 includes deploying one or more image interpretation protocols when the deployment rate decreases below the threshold. Method 400 then returns.

Returning to 412, if the deployment rate is not greater than the threshold deployment rate, method 400 proceeds to 428. At 428, method 400 includes operating the scanning in the static mode, wherein turbulence due to one or more of probe and patient movement is less. Accordingly, operating the scanning in the static mode includes, at 430, performing the scan while deploying the one or more desired image interpretation protocols. As discussed herein, the image interpretation protocols may include artificial intelligence based protocols implemented based on deep-learning models and image processing protocols that can be implemented without employing deep-learning models. Further, operating the scanning in the static mode includes, at 432, continuing turbulence monitoring between successive frames of the acquired sequence while deploying one or more desired image interpretation protocols. Method 400 then returns.

In this way, by monitoring the AI based algorithm deployment rate, efficiency of ultrasound scanning may be improved. Further, in some embodiments, when the algorithm deployment rate is high (greater than the threshold deployment rate), non-AI based algorithms may be used to provide guidance to the user.

In one embodiment, a user calibration may be performed at the beginning of an ultrasound scan, prior to imaging the patient, to determine an expected amount of turbulence that may be introduced due to unsteady probe movement by the user. For example, for a novice user, the user calibration may indicate a higher amount of expected turbulence caused by the probe movement compared to an experienced user. The user calibration may be performed on a phantom, and the expected amount of turbulence may be determined based on a selected performance metric calculated between successive frames or between a reference frame and one or more successive frames. The performance metric may be consistent with the performance metric used for determining the amount of turbulence during ultrasound scanning of the patient. Based on the expected amount of turbulence, one or more thresholds for AI algorithm deployment during actual ultrasound scanning with the patient may be set. As an example, for a novice user, the expected amount of turbulence may be higher, and as such, the second higher threshold may be lowered, so as to ensure improved ultrasound scanning quality. Further, the user calibration may also provide an indication that the user is a novice user based on the expected amount of turbulence. Accordingly, certain image interpretation protocols that may be used to improve guidance to the user but does not need higher quality image sequences may be deployed during scanning conditions when deployment of AI based image interpretation protocols is not permitted.

For an experienced user, the probe movement may be steadier. As a result, the expected amount of turbulence may be lower, and as such, during scanning the amount of turbulence may be expected to be within the second higher threshold. Accordingly, the second higher threshold and the first lower threshold may be increased so that AI based image interpretation algorithms remain deployed without much interruption to further improve ultrasound scanning efficiency for the experienced user.

Turning to FIG. 5, an example ultrasound scanning sequence including time periods when one or more image interpretation protocols are deployment based on an amount of turbulence is shown. Specifically, deployment of one or more artificial intelligence protocols for image interpretation and analysis, such as deep-learning based segmentation, labelling, identification, classification, biometry, and anomaly tracking, based on turbulence and turbulence frequency is shown. The deployment of one or more image interpretation protocols shown in FIG. 5 may be performed according to method 300 discussed in FIGS. 3A and 3B using the ultrasound system discussed in FIGS. 1-2. Vertical markers t1-t5 represent times of interest during the scanning sequence.

FIG. 5 illustrates an example status of user and/or patient alert indication, for example, at a user interface of an ultrasound monitoring system and/or via audible alerts, at plot 502; turbulence frequency based on a frequency of oscillation of a normalized structural similarity metric at plot 504; a threshold turbulence frequency at 505; an amount of turbulence at plot 506; a first lower threshold 509; a second higher threshold 507; the normalized similarity metric at plot 510; and a status of AI based algorithm deployment at plot 512.

The first plot from the top of FIG. 5 is a plot of user and/or patient alert status versus time. The Y-axis represents an ON/OFF status of the alert.

The second plot from the top of FIG. 5 is a plot of turbulence frequency versus time. The Y-axis represents turbulence frequency and the frequency increases in the direction of Y-axis arrow.

The third plot from the top of FIG. 5 is a plot of the amount of turbulence versus time. The Y-axis represents the amount of turbulence and the amount of turbulence increases in the direction of Y-axis arrow.

The fourth plot from the top of FIG. 5 is a plot of the normalized structural similarity metric versus time. The Y-axis represents the normalized structural similarity metric and normalized value of the structural similarity metric increases from zero to one in the direction of Y-axis arrow.

The fifth plot from the top of FIG. 5 is a plot of AI based algorithm deployment status versus time. The Y-axis represents an ON/OFF status of the algorithm deployment status.

At t0, the structural similarity metric may have a high value (plot 510), indicating high structural similarity between two successive image frames or between the reference frame and each of one or more successive frame following the reference frame. Consequently, the amount of turbulence (plot 506) is below the first lower threshold 509. In response to the amount of turbulence below the first lower threshold at t0, the one or more AI based algorithms may be deployed shortly after t0. The amount of turbulence may continue to be monitored after AI algorithm deployment. Between time of AI algorithm deployment (after t0) and t1, the image quality may be high due to reduced probe movement and reduced periodic motion of the anatomical structure under examination. As a result, the structural similarity metric may remain high (plot 510), and the amount of turbulence (plot 506) may be below the first lower threshold 509. Consequently, one or more artificial intelligence protocols for image interpretation and analysis may remain deployed.

Between t1 and t2, periodic motion, such as due to breathing, may be observed during scanning (for example, due to examination of an anatomical structure, such as lungs, the structure of which undergoes changes based on the physiological function performed, such as breathing). The periodic motion, even under a steady state condition, may show a decrease the image quality, particularly when the reference image and the successive image compared do not show high structural similarity. However, during the periodic motion, when the reference frame matches the successive image frame, the value of the normalized structural similarity metric reaches a peak, and thus, periodic motion may be determined by the processor by monitoring periodic peaks and troughs in the structural similarity metric during the scanning. Between t1 and t2, the periodic motion may be in a steady state, and hence a frequency of periodic motion (turbulence frequency) determined based on the frequency of the sine-wave pattern of the normalized structural similarity (plot 510). Since the periodic motion is in a steady state, the turbulence frequency (504) may be below threshold frequency 505. Thus, even when the amount of turbulence (plot 506) increases above the first lower threshold 509, the scanning is performed in a steady state (as determined by low frequency of oscillation of the normalized structural similarity metric) and amount of turbulence below the second higher threshold 507. As a result, the AI algorithms may continue to be deployed (plot 512). Further, between t0 and t1, one or more audible and visual alerts may not be provided in response to high image quality and steady state scanning.

Between, t2 and t3, rapid breathing may occur. As a result, the turbulence frequency (plot 504) may increase above threshold 505 even while the amount of turbulence (plot 506) remains below the second higher threshold 507. In response to the threshold rate greater than the threshold, deployment of the one or more artificial intelligence protocols for image interpretation and analysis may be terminated (plot 512) until the image quality improves. Further an indication to the user to request the patient to hold breath or maintain steady breath may be provided. The time period between t3 and t4 may be similar to t1 and t2, during which the rapid periodic motion has subsided and a more steady motion is achieved. Accordingly, one or more artificial intelligence protocols for image interpretation and analysis may be deployed again.

Between t4 and t5, the image quality may degrade, for example due to improper probe positioning and/or movement. Consequently, the amount of turbulence (plot 506) is higher than the second higher threshold 507. In response to the turbulence increasing above the second threshold 507, deployment of the one or more artificial intelligence protocols for image interpretation and analysis may be terminated (plot 512). Further, an indication to the user to adjust probe position and/or movement may be provided (plot 502). Deployment of the one or more artificial intelligence protocols for image interpretation and analysis may resume when the turbulence decreases (at t5 and for some duration after t5 during the scan) and the image quality increases.

In this way, deployment of one or more AI based algorithms may be determined based on real-time monitoring image quality by using a structural similarity metric during ultrasound scanning. Thus, the turbulence and/or image quality monitoring acts as a gate-keeper for one or more image interpretation algorithms deploying them only when the image quality is greater than a threshold and when temporal turbulence is below the threshold turbulence, and further provides one or more alerts to the user regarding the presence of turbulence and potential solutions for reducing turbulence.

The technical effect of using the turbulence monitoring method is increased confidence and reduced error in artificial intelligence based image interpretation algorithms including artificial intelligence based segmentation, labelling, identification, biometry, and classification algorithms. Another technical effect of deploying artificial intelligence based algorithms only when high frequency variations introduced by one or more of anatomical motion and probe motion subsides, is increased reliability on artificial intelligence based algorithms. Yet another technical effect of controlling deployment of artificial intelligence based algorithms is improved anatomy labelling overlaid on the images. Another technical effect of deploying artificial intelligence based algorithms based on turbulence monitoring is overall improved efficiency of ultrasound scanning, and reduced consumption of non-transitory memory resources when conditions are not favorable for AI deployment. Further, one or more alerts and guidance provided based on turbulence monitoring additionally increases efficiency and quality of ultrasound scanning.

An embodiment for a method for a medical imaging processor includes during an ultrasound scan, evaluating image quality between two scan images, and deploying one or more image interpretation algorithms only when the image quality is above a threshold. A first example of the method includes during the ultrasound scan with the one or more image interpretation algorithms deployed, when the image quality is below the threshold, stopping deployment of the one or more image interpretation algorithms and providing one or more alerts via a user interface. In a second example of the method, which optionally includes the first example, and further includes wherein the one or more alerts include a first indication of turbulence during the scanning and a second indication including providing instructions to one or more of a user to hold an ultrasound probe steady and a patient to hold breath. In a third example of the method, which optionally includes one or both of the first and second examples, the method further includes wherein evaluating the image quality includes determining a structural similarity metric between the two scan images. In a fourth example of the method, which optionally includes one or more or each of the first through third examples, the method further includes wherein the structural similarity metric is any of Structural Similarity Index Metric (SSIM), Mean Square Error (MSE), Peak Signal to Noise Ratio (PSNR), Equivalent Number of Looks (ENL) and Edge preservation Index (EPI), multi-scale SSIM, complex wavelet SSIM, and three-component SSIM. In a fifth example of the method, which optionally includes one or more or each of the first through fourth examples, the method further includes wherein evaluating the image quality includes determining a structural similarity metric between a selected region of interest in each of the two images. In a sixth example of the method, which optionally includes one or more or each of the first through fifth examples, the method includes wherein the one or more image interpretation algorithms include one or more artificial intelligence based algorithms; and wherein the one or more artificial intelligence based algorithms include deep neural network based algorithms for one or more of image segmentation, tracking, and biometry. In a seventh example of the method, which optionally includes one or more or each of the first through sixth examples, the method further includes during ultrasound scanning, when the image quality is below the threshold, deploying the one or more image interpretation algorithms if a frequency of change of image quality over a sequence of scan images is within a threshold frequency.

An embodiment is directed to a method for a medical imaging processor including during scanning with an ultrasound probe, monitoring a turbulence amount between a first scan image and a second scan image; in response to the turbulence amount below a higher threshold, deploying one or more image interpretation algorithms; and in response to the turbulence amount above the higher threshold, stopping deployment of the one or more image interpretation algorithms and providing an alert via a user interface. A first example of the method includes wherein the turbulence amount is based on an amount of structural similarity between the first image and the second image; and wherein the turbulence amount increases as the structural similarity decreases. In a second example of the method, which optionally includes the first example, and further includes wherein the amount of structural similarity is determined based on a structural similarity metric; and wherein the structural similarity metric is any of a Structural Similarity Index Metric (SSIM), Mean Square Error (MSE), Peak Signal to Noise Ratio (PSNR), Equivalent Number of Looks (ENL) and Edge preservation Index (EPI), multi-scale SSIM, complex wavelet SSIM, and three-component SSIM. In a third example of the method, which optionally includes one or both of the first and second examples, the method further includes wherein the one or more alerts includes a guidance to a user operating the ultrasound probe to hold the probe steady. In a fourth example of the method, which optionally includes one or more or each of the first through third examples, the method further includes wherein the one or more image interpretation algorithms include one or more artificial intelligence based algorithms; and wherein the one or more artificial intelligence based algorithms include deep neural network based algorithms for one or more of image segmentation, tracking, and biometry. In a fifth example of the method, which optionally includes one or more or each of the first through fourth examples, the method further includes during scanning with an ultrasound probe, monitoring a turbulence amount between a first scan image and a second scan image; in response to the turbulence amount below a higher threshold, deploying one or more image interpretation algorithms; and in response to the turbulence amount at or above the higher threshold, stopping deployment of the one or more image interpretation algorithms and providing an alert via a user interface. In a sixth example of the method, which optionally includes one or more or each of the first through fifth examples, the method includes wherein the turbulence frequency for the scan duration is determined based on a structural similarity metric of a sequence of plurality of scan images with respect to a reference scan image. In a seventh example of the method, which optionally includes one or more or each of the first through sixth examples, the method further includes providing a different alert when the turbulence frequency is greater than the threshold frequency; and wherein the different alert includes a second guidance indicating a patient under examination to hold breath.

An embodiment for turbulence monitoring in a medical imaging system is provided. The imaging system includes an ultrasound probe; a user interface including a display portion; and a processor configured with instructions in non-transitory memory that when executed cause the processor to: acquire a sequence of ultrasound scan images generated based on scan data from the ultrasound probe; monitor an amount of turbulence between at least two successive scan images from the sequence of ultrasound scan images; and responsive to the amount of turbulence less than a threshold amount, deploying one or more image interpretation algorithms. In a first example of the system, the processor is further configured with instructions in non-transitory memory for: responsive to the amount of turbulence at or above the threshold amount, continuing acquiring scan images without deploying one or more image interpretation algorithms, and providing one or more alerts via a user interface; and wherein the one or more alerts include an indication of a turbulent scanning and one or more instructions to hold probe steady and to hold breath for a short duration. In a second example of the imaging system, which optionally includes the first example, the amount of turbulence is determined based on an image quality metric; and wherein the image quality metric is any of a Structural Similarity Index Metric (SSIM), Mean Square Error (MSE), Peak Signal to Noise Ratio (PSNR), Equivalent Number of Looks (ENL) and Edge preservation Index (EPI), multi-scale SSIM, complex wavelet SSIM, and three-component SSIM. In a third example of the imaging system, which optionally includes one or both of the first and second examples, the one or more image interpretation algorithms include one or more artificial intelligence based algorithms; and wherein the one or more artificial intelligence based algorithms include deep neural network based algorithms for one or more of image segmentation, tracking, and biometry.

One or more specific embodiments of the present disclosure are described above in order to provide a thorough understanding. These described embodiments are only examples of systems and methods for evaluating structural similarity between at least two anatomical structures by using a deep learning model implementing a plurality of neural network models. The skilled artisan will understand that specific details described in the embodiments can be modified when being placed into practice without deviating the spirit of the present disclosure.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements.

Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for a medical imaging processor, comprising:
during an ultrasound scan, evaluating a rate of change in content across a temporal sequence of images, and deploying one or more image interpretation algorithms only when the rate of change is below a threshold; and
during the ultrasound scan with the one or more image interpretation algorithms deployed, when the rate of change in content across the temporal sequence of images is above the threshold, stopping deployment of the one or more image interpretation algorithms and providing one or more alerts via a user interface,
wherein the one or more alerts include a first indication of turbulence that indicates a high rate of change of content across the temporal sequence of images during the scanning and a second indication including providing instructions to either or both of a user to hold an ultrasound probe steady and a patient to hold breath.

2. The method of claim 1, wherein evaluating the rate of change in content across the temporal sequence of images includes determining a structural similarity metric between two scan images.

3. The method of claim 2, wherein the structural similarity metric is any of Structural Similarity Index Metric (SSIM), Mean Square Error (MSE), Peak Signal to Noise Ratio (PSNR), Equivalent Number of Looks (ENL) and Edge preservation Index (EPI), multi-scale SSIM, complex wavelet SSIM, and three-component SSIM.

4. The method of claim 1, wherein evaluating the rate of change in content across the temporal sequence of images includes determining a structural similarity metric between a selected region of interest in each of the two images.

5. The method of claim 1, wherein the one or more image interpretation algorithms include one or more artificial intelligence based algorithms; and
wherein the one or more artificial intelligence based algorithms include deep neural network based algorithms for either or both of image segmentation and biometry.

6. A method for a medical imaging processor, comprising:
during scanning with an ultrasound probe,
monitoring a turbulence amount between a first scan image and a second scan image;
in response to the turbulence amount below a higher threshold, deploying one or more image interpretation algorithms;
in response to the turbulence amount above the higher threshold, stopping deployment of the one or more image interpretation algorithms and providing an alert via a user interface;
in response to the turbulence amount above a lower threshold and below the higher threshold, determining a turbulence frequency for a scan duration, and stopping deployment of the one or more image interpretation algorithms when the turbulence frequency is greater than a threshold frequency; and
in response to the turbulence amount below the lower threshold, deploying the one or more image interpretation algorithms.

7. The method of claim 6, wherein the turbulence amount is based on an amount of structural similarity between the first image and the second image;
and wherein the turbulence amount increases as the structural similarity decreases.

8. The method of claim 7, wherein the amount of structural similarity is determined based on a structural similarity metric; and wherein the structural similarity metric is any of a Structural Similarity Index Metric (SSIM), Mean Square Error (MSE), Peak Signal to Noise Ratio (PSNR), Equivalent Number of Looks (ENL) and Edge preservation Index (EPI), multi-scale SSIM, complex wavelet SSIM, and three-component SSIM.

9. The method of claim 6, wherein the one or more alerts includes a guidance to a user operating the ultrasound probe to hold the ultrasound probe steady.

10. The method of claim 6, wherein the one or more image interpretation algorithms include one or more artificial intelligence based algorithms; and
wherein the one or more artificial intelligence based algorithms include deep neural network based algorithms for either or both of image segmentation and biometry.

11. The method of claim 6, wherein the turbulence frequency for the scan duration is determined based on a structural similarity metric of a sequence of plurality of scan images with respect to a reference scan image.

12. The method of claim 6, further comprising providing a different alert when the turbulence frequency is greater than the threshold frequency; and
wherein the different alert includes a guidance indicating a patient under examination to hold breath.

13. An imaging system, comprising:
an ultrasound probe;
a user interface including a display portion; and
a processor configured with instructions in non-transitory memory that when executed cause the processor to:
acquire a sequence of ultrasound scan images generated based on scan data from the ultrasound probe;
monitor an amount of turbulence between at least two successive scan images from the sequence of ultrasound scan images;
responsive to the amount of turbulence less than a threshold amount, deploying one or more image interpretation algorithms; and
responsive to the amount of turbulence at or above the threshold amount, continuing acquiring scan images without deploying one or more image interpretation algorithms, and providing one or more alerts via a user interface; and wherein the one or more alerts include an indication of a turbulent scanning and one or more instructions to hold probe steady and to hold breath for a short duration.

14. The system of claim 13, wherein the amount of turbulence is determined based on an image quality metric; and wherein the image quality metric is any of a Structural Similarity Index Metric (SSIM), Mean Square Error (MSE), Peak Signal to Noise Ratio (PSNR), Equivalent Number of Looks (ENL) and Edge preservation Index (EPI), multi-scale SSIM, complex wavelet SSIM, and three-component SSIM.

15. The system of claim 13, wherein the one or more image interpretation algorithms include one or more artificial intelligence based algorithms; and wherein the one or more artificial intelligence based algorithms include deep neural network based algorithms for either or both of image segmentation and biometry.

* * * * *